US00PP32593P2

(12) United States Plant Patent
Rinehart

(10) Patent No.: US PP32,593 P2
(45) Date of Patent: Dec. 8, 2020

(54) POINSETTIA PLANT NAMED 'RINEAB'

(50) Latin Name: ***Euphorbia pulcherrima* Willd.**
Varietal Denomination: Rineab

(71) Applicant: Steven Earl Rinehart, Encinitas, CA (US)

(72) Inventor: Steven Earl Rinehart, Encinitas, CA (US)

( * ) Notice: Subject to any disclaimer, the term of this patent is extended or adjusted under 35 U.S.C. 154(b) by 0 days.

(21) Appl. No.: 16/873,265

(22) Filed: Mar. 6, 2020

(51) Int. Cl.
*A01H 5/02* (2018.01)
*A01H 6/38* (2018.01)

(52) U.S. Cl.
USPC ..... Plt./307
CPC ..... *A01H 6/38* (2018.05)

(58) Field of Classification Search
USPC ..... Plt./307
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'Rineab', characterized by its upright and uniformly mounded plant habit; moderately vigorous growth habit; freely and upright to somewhat outwardly branching habit with thick and sturdy lateral branches; dark green-colored leaves that are oak leaf-shaped; early flowering habit; inflorescences with vivid red-colored flower bracts that are oak leaf-shaped; and good post-production longevity.

2 Drawing Sheets

Figure 1:
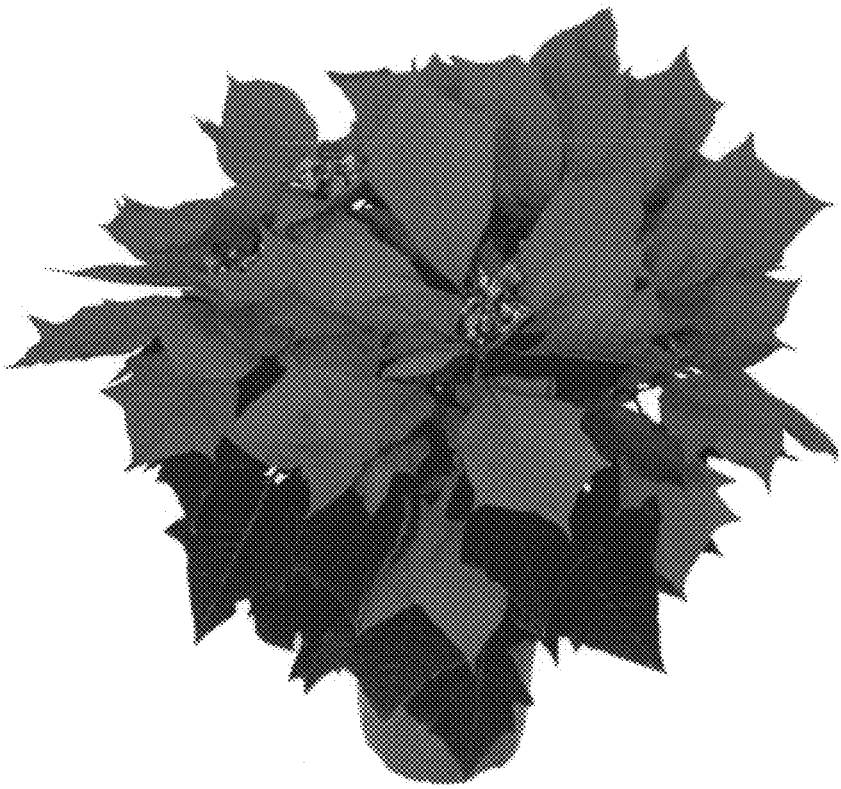
Figure 2:
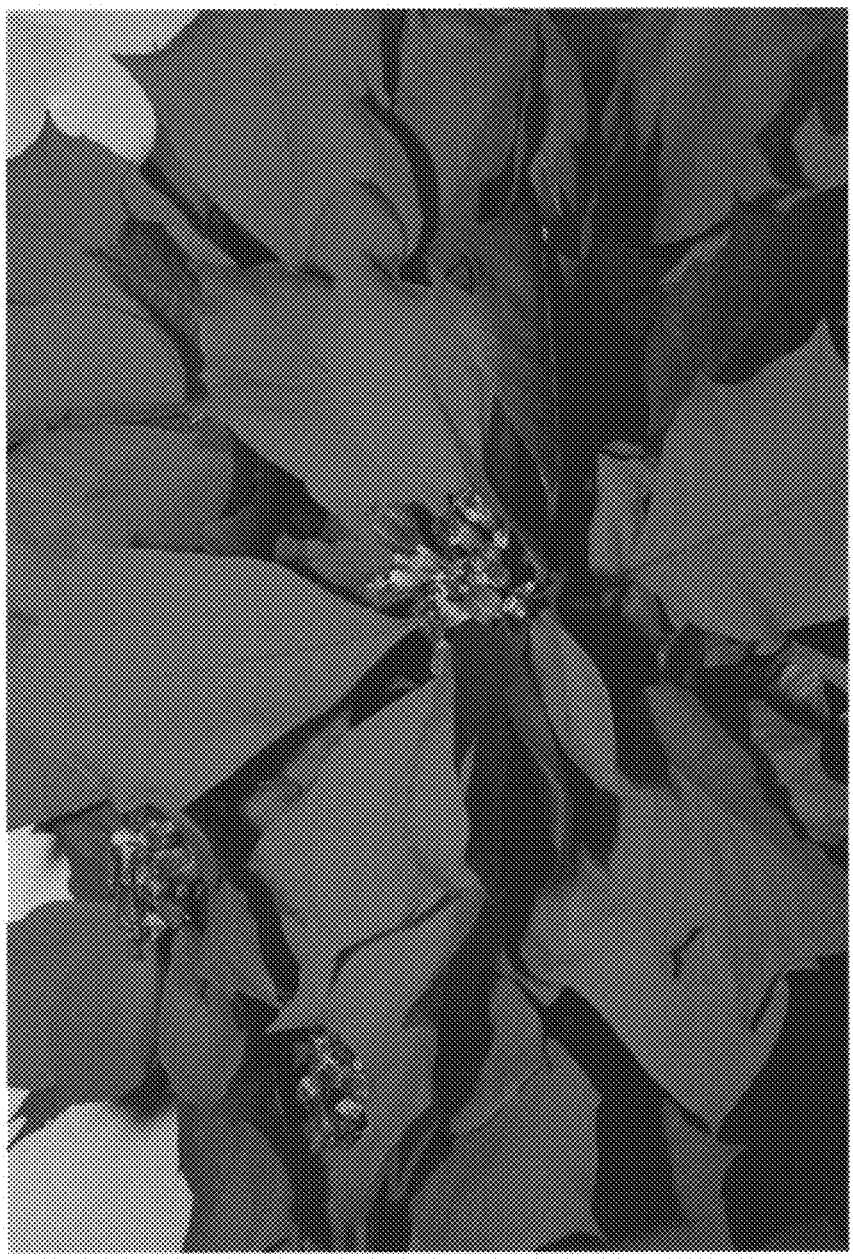

Botanical designation: *Euphorbia pulcherrima* Willd.
Cultivar denomination: 'RINEAB'.

BACKGROUND OF THE INVENTION

The present invention relates to a new and distinct cultivar of Poinsettia plant, botanically known as *Euphorbia pulcherrima* Willd., and hereinafter referred to by the cultivar name 'Rineab'.

The new Poinsettia plant is a product of a planned breeding program conducted by the Inventor in Bonsall, Calif. The objective of the breeding program is to create new strong, upright and early-flowering Poinsettia plants having upright flower bracts, good cyathia development, high temperature tolerance and excellent post-production longevity.

The new Poinsettia plant originated from a cross-pollination made by the Inventor in the autumn of 2013 of *Euphorbia pulcherrima* Willd. 'Dueavared', disclosed in U.S. Plant Pat. No. 18,627, as the female, or seed, parent, with *Euphorbia pulcherrima* Willd. 'PER1360', disclosed in U.S. Plant Pat. No. 28,222, as the male, or pollen, parent. The new Poinsettia plant was discovered and selected by the Inventor as a single flowering plant from within the progeny of the stated cross-pollination in a controlled greenhouse environment in Bonsall, Calif. in November, 2014.

Asexual reproduction of the new Poinsettia plant by terminal vegetative cuttings in a controlled greenhouse environment in Bonsall, Calif. since the spring of 2015 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Rineab'. These characteristics in combination distinguish 'Rineab' as a new and distinct Poinsettia plant:

1. Upright and uniformly mounded plant habit.
2. Moderately vigorous growth habit.
3. Freely and upright to somewhat outwardly branching habit with thick and sturdy lateral branches.
4. Dark green-colored leaves that are oak leaf-shaped.
5. Early flowering habit; when grown under natural flowering season conditions plants flower on or about November 28 in Southern California.
6. Inflorescences with vivid red-colored flower bracts that are oak leaf-shaped.
7. Good post-production longevity.

In side-by-side comparisons conducted in Bonsall, Calif., plants of the new Poinsettia differ primarily from plants of the female parent, 'Dueavared', in the following characteristics:

1. Branch angle of plants of the new Poinsettia is more upright than and not as wide as branch angle of plants of 'Dueavared'.
2. Plants of the new Poinsettia have thicker stems than plants of 'Dueavared'.
3. Leaves of plants of the new Poinsettia are broader than leaves of plants of 'Dueavared'.
4. Leaves of plants of the new Poinsettia are oak leaf-shaped whereas leaves of plants of 'Dueavared' are ovate in shape.
5. Flower bracts of plants of the new Poinsettia are broader than flower bracts of plants of 'Dueavared'.
6. Flower bracts of plants of the new Poinsettia are oak leaf-shaped whereas flower bracts of plants of 'Dueavared' are ovate in shape.

7. Flower bracts of plants of the new Poinsettia are lighter red in color than flower bracts of plants of 'Dueavared'.

In side-by-side comparisons conducted in Bonsall, Calif., plants of the new Poinsettia differ primarily from plants of the male parent, 'PER1360', in the following characteristics:

1. Plants of the new Poinsettia are taller than plants of 'PER1360'.
2. Branch angle of plants of the new Poinsettia is more upright than and not as wide as branch angle of plants of 'PER1360'.
3. Leaves of plants of the new Poinsettia are oak leaf-shaped whereas leaves of plants of 'PER1360' are ovate in shape occasionally with broad lobes.
4. Flower bracts of plants of the new Poinsettia are oak leaf-shaped whereas flower bracts of plants of 'PER1360' are ovate in shape occasionally with broad lobes.
5. Flower bracts of plants of the new Poinsettia are more upright than flower bracts of plants of 'PER1360'.
6. Flower bracts of plants of the new Poinsettia are lighter red in color than flower bracts of plants of 'PER1360'.

Plants of the new Poinsettia can be compared to plants of the *Euphorbia pulcherrima* Willd. 'Eckanezka', disclosed in U.S. Plant Pat. No. 19,192. In side-by-side comparisons, plants of the new Poinsettia differ primarily from plants of 'Eckanezka' in the following characteristics:

1. Plants of the new Poinsettia are more upright and taller than plants of 'Eckanezka'.
2. Leaves of plants of the new Poinsettia are broader than leaves of plants of 'Eckanezka'.
3. Leaves of plants of the new Poinsettia are oak leaf-shaped whereas leaves of plants of 'Eckanezka' are ovate to elliptical in shape.
4. Flower bracts of plants of the new Poinsettia are oak leaf-shaped whereas flower bracts of plants of 'Eckanezka' are ovate to elliptical in shape.
5. Flower bracts of plants of the new Poinsettia are lighter red in color than flower bracts of plants of 'Eckanezka'.
6. Plants of the new Poinsettia are more high temperature tolerant than plants of 'Eckanezka'.

Plants of the new Poinsettia can also be compared to plants of the *Euphorbia pulcherrima* Willd. 'PER1055', disclosed in U.S. Plant Pat. No. 15,882. In side-by-side comparisons, plants of the new Poinsettia differ primarily from plants of 'PER1055' in the following characteristics:

1. Leaves of plants of the new Poinsettia are oak leaf-shaped whereas leaves of plants of 'PER1055' are elliptical in shape.
2. Flower bracts of plants of the new Poinsettia are oak leaf-shaped whereas flower bracts of plants of 'PER1055' are elliptical in shape.
3. Flower bracts of plants of the new Poinsettia are flatter than and not as undulate as flower bracts of plants of 'PER1055'.
4. Flower bracts of plants of the new Poinsettia are lighter red in color than flower bracts of plants of 'PER1055'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet (FIG. 1 of 2) is a side perspective view of a typical flowering plant of 'Rineab' grown in a 15.25-cm container.

The photograph on the second sheet is a close-up view of a typical flowering plant of 'Rineab'.

DETAILED BOTANICAL DESCRIPTION

Plants used in the aforementioned photographs and in the following detailed description were grown during the spring and summer in 15.25-cm in a polyethylene-covered greenhouses in Bonsall and Encinitas, Calif. under artificial long nyctoperiod conditions and cultural practices typical of commercial Poinsettia production. During the production of the plants, day temperatures averaged 26° C., night temperatures averaged 18° C. and light levels averaged 4,500 foot-candles. Measurements and numerical values represent averages for typical flowering plants. Plants were pinched one time two weeks after planting and were 18 weeks from unrooted cuttings when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'Rineab'.

Parentage:

*Female, or seed, parent.*—*Euphorbia pulcherrima* Willd. 'Dueavared', disclosed in U.S. Plant Pat. No. 18,627.

*Male, or pollen, parent.*—*Euphorbia pulcherrima* Willd. 'PER1360', disclosed in U.S. Plant Pat. No. 28,222.

Propagation:

*Type.*—Terminal vegetative cuttings.

*Time to initiate roots, summer.*—About ten days to develop root callus and about 15 days for root initiation at night temperatures about 18° C.

*Time to produce a rooted young plant, summer.*—About four weeks at night temperatures about 18° C.

*Root description.*—Thick, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright and uniformly mounded plant habit; inverted triangle; medium-sized inflorescences with numerous flower bracts positioned above the foliar plane; moderately vigorous growth habit and moderate growth rate.

*Plant height.*—About 32 cm.

*Plant diameter or spread.*—About 42 cm.

*Lateral branch description.*—Branching habit: Freely branching habit, about nine lateral branches develop after pinching; upright to somewhat outwardly branching habit. Length: About 27 cm. Diameter: About 6 mm. Internode length: About 1.5 cm. Strength: Strong. Aspect: About 30° to 45° from vertical. Texture and luster: Smooth, glabrous; matte. Color: Close to 146B.

*Leaf description*.—Arrangement: Alternate, simple. Length: About 10 cm. Width: About 9.1 cm. Shape: Oak leaf-shaped, three to five-lobed. Apex: Acuminate. Base: Attenuate. Margin: Relatively deeply lobed. Aspect: Slightly upright to outwardly; flat. Texture and luster, upper surface: Sparse pubescence along venation; matte. Texture and luster, lower surface: Sparsely pubescent; prominent venation; matte. Venation pattern: Pinnate, arcuate. Color: Developing leaves, upper surface: Close to 146A. Developing leaves, lower surface: Close to 146B. Fully expanded leaves, upper surface: Darker than 147A; venation, close to 146A. Fully expanded leaves, lower surface: Close to N137B; venation, close to 147C. Leaf petioles: Length: About 5.8 cm. Diameter: About 2.5 mm. Texture and luster, upper and lower surfaces: Smooth, glabrous; moderately glossy. Color, upper surface: Close to 185A. Color, lower surface: Close to 146C.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower on or about November 28 in Southern California; under artificial long nyctoperiod/short photoperiod conditions, plants flower about 8.5 weeks later.

*Post-production longevity*.—Good post-production longevity; plants of the new Poinsettia maintain good substance and flower bract color for about two months under interior conditions; flower bracts persistent and cyathia not persistent.

*Inflorescence diameter*.—About 28 cm.

*Inflorescence height* (*depth*).—About 9.5 cm to 10 cm.

*Flower bracts*.—Quantity per inflorescence: Numerous, about 28. Length, largest bracts: About 11.5 cm. Width, largest bracts: About 8 cm. Shape: Oak leaf-shaped, three to five-lobed. Apex: Acuminate. Base: Attenuate. Margin: Relatively deeply lobed. Aspect: Somewhat upright to becoming mostly horizontal to slightly drooping with development. Texture and luster, upper surface: Smooth, glabrous; matte. Texture and luster, lower surface: Glabrous with prominent venation; matte. Venation pattern: Pinnate, arcuate. Color: Transitional bracts, upper surface: Close to 183A to 183B, 53A and 53B. Transitional bracts, lower surface: Close to 146B overlain with close to 183C. Developing bracts, upper surface: Close to 45A. Developing bracts, lower surface: Close to 45C. Fully expanded bracts, upper surface: Close to 45A; color becoming closer to 47A with development. Fully expanded bracts, lower surface: Close to 45C; color becoming closer to 47A with development. Bract petioles: Length: About 2.7 cm. Diameter: About 2 mm. Texture and luster, upper and lower surfaces: Smooth, glabrous; matte. Color, upper surface: Close to 46A. Color, lower surface: Close to 46B overlain with close to 53B.

*Cyathia*.—Quantity per corymb: About 15. Length: About 1.6 cm. Width: About 6 mm. Shape: Ovoid. Texture and luster: Smooth, glabrous; matte. Color, inner surface: Close to 145A. Color, outer surface: Close to 146B to 146C.

*Nectaries*.—Quantity per cyathium: One. Length: About 4 mm. Width: About 2 mm. Shape: Roughly elliptical. Texture and luster: Smooth, glabrous; matte. Color, developing, inner and outer surfaces: Close to 3B. Color, fully developed, inner and outer surfaces: Close to 21A.

*Peduncles*.—Length: About 5 mm. Diameter: About 3 mm. Strength: Strong. Aspect: Mostly upright to outwardly. Texture and luster: Smooth, glabrous; matte. Color: Close to 145A.

*Reproductive organs*.—Stamens: Quantity per cyathium: About five to ten. Filament length: About 4 mm. Filament color: Close to 187B. Anther shape: Round to oval; bi-lobed. Anther length: About 1 mm. Anther color: Close to 187B. Amount of pollen: Scarce. Pollen color: Close to 9B. Pistils: Quantity per cyathium: One; tri-parted. Pistil length: About 9 mm. Stigma shape: Lanceolate, six-parted, recurved. Stigma color: Close to 187B. Style length: About 2 mm. Style color: Close to 145C. Ovary color: Close to 144B.

*Seeds and fruits*.—To date, seed and fruit production have not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 16° C. to about 32° C.

It is claimed:

1. A new and distinct Poinsettia plant named 'Rineab' as illustrated and described.

* * * * *